United States Patent [19]
Eagan

[11] Patent Number: 5,435,185
[45] Date of Patent: Jul. 25, 1995

[54] ELECTRONIC INSTRUMENT FOR LOCATING AND DIAGNOSING AUTOMOTIVE CHASSIS SOUNDS

[76] Inventor: Chris S. Eagan, 670 Eldorado La., Las Vegas, Nev. 89123

[21] Appl. No.: 106,440

[22] Filed: Aug. 16, 1993

[51] Int. Cl.⁶ .......................................... G01N 29/00
[52] U.S. Cl. ...................................... 73/587; 73/584; 73/592
[58] Field of Search ............... 73/587, 660, 661, 593, 73/592, 40.5 A, 584; 439/504

[56] References Cited

U.S. PATENT DOCUMENTS

| | | | |
|---|---|---|---|
| 3,365,935 | 1/1968 | Kane | 73/661 |
| 4,287,581 | 9/1981 | Neale, Sr. | 73/40.5 A |
| 4,583,405 | 4/1986 | Simmons | 73/661 |
| 4,583,406 | 4/1986 | Dimeff | 73/40.5 A |
| 4,790,191 | 12/1988 | Shultz, Jr. | 73/660 |
| 4,809,554 | 3/1989 | Shade et al. | 73/587 |

OTHER PUBLICATIONS

"5100 Series Leak Monitoring and Detection System"; Physical Acoustics Corporation; 1984; pp. 1-4.

Primary Examiner—Hezron E. Williams
Assistant Examiner—Helen C. Kwok
Attorney, Agent, or Firm—Philip D. Junkins

[57] ABSTRACT

A vibration and acoustic sound diagnostic instrument for use by a professional automotive maintenance mechanic which is capable of discriminating audible vibration sound and noise generated by under-chassis and under-hood parts and devices having mechanical faults. The instrument includes at least one acoustic vibration pick-up device adapted for mounting in contact with an automotive part or device for detecting and converting vibratory acoustic signals and sounds into electromagnetic signals and an electronics housing conformed to be held in the hand of the maintenance mechanic. Pre-amplifier circuitry within the housing is electrically coupled to the acoustic vibration pick-up device and to range selector circuitry for selecting sound level ranges respecting the electromagnetic signals. A decibel meter, mounted to the exterior of the housing, is electrically interconnected to the pre-amplifier for visually indicating changes and peaks in the sound levels detected by the transducer microphone. Operational audio amplifier circuitry within the housing is electrically interconnected to the pre-amplifier circuitry for converting the electromagnetic signals into secondary acoustic signals that may be listened to by the maintenance mechanic through an earphone headset electrically interconnected to the audio amplifier. The instrument is energized by a battery power supply contained within the housing.

14 Claims, 2 Drawing Sheets

ELECTRONIC INSTRUMENT FOR LOCATING AND DIAGNOSING AUTOMOTIVE CHASSIS SOUNDS

BACKGROUND OF THE INVENTION

1. Field of the Invention

The present invention relates to a method and instrumentation for detecting, locating and diagnosing automotive chassis sounds. More particularly, the invention is directed to electronic diagnostic instrumentation for locating the source and cause, in automotive vehicles, of under-chassis, under-hood and under-dash problem sounds and noise. The instrumentation is most suitable for use by automotive repair and service personnel.

2. Description of The Prior Art

The modern automotive vehicle, whether a passenger automobile, recreational vehicle, pick-up truck, delivery van or large semitrailer, presents a complex conglomeration of engine, power transmission, differential, wheels and bearings, and associated machinery and devices that each present a potential for problems with the resulting generation of vibrations, sounds and noise. Today's automotive vehicle manufacturers stress that their driver and passenger compartments are "sound proof" and this factor multiplies the problem of locating under-chassis, under-hood and under-dash mechanical sounds and noise (including squeaks and rattles) generated by faulty and improperly functioning automotive machinery and parts.

It has been well known to use mechanical vibration detectors as a means for determining whether, or where it is, that an automotive vehicle needs repair or adjustment to assure optimum operation. One such device, called a "Vibrameter," has been manufactured by SPM Instrument, Inc. of Wallingford, Conn. and includes a piezoelectric device attached to a vibrating automotive part and converts the vibrations to an electrical signal in digital form that is displayed on a hand-held device. Another similar device, also manufactured by SPM Instrument, Inc., is called the "Electronic Stethoscope" and includes a hand-held device having an elongated probe capable of being placed against a vibrating machine part and connected through a piezoelectric unit for converting the detected vibrations into an electrical signal which is amplified through earphones so that the vibrations are detected as a noise level.

In December of 1988, U.S. Pat. No. 4,790,191 was granted to W.L. Shultz, Jr. for "Comparative Mechanical Fault Detection Apparatus and Clamp." The Shultz patent is directed to apparatus for determining a mechanical fault in an automotive vehicle by determining mechanical vibration comparatively between two like devices of the vehicle to determine which of the two devices is in need of repair or replacement. The apparatus includes two piezoelectric vibration sensors operatively secured to a pair of mechanical clamps capable of being attached to two like devices of the vehicle such as a pair of McPherson struts interconnected through metal parts to two front wheel bearing assemblies. The first and second piezoelectric sensors are operatively and alternatively connected electrically to an indicator device for producing an electrical signal amplitude proportional to mechanical vibration whereby the operator of the apparatus can audibly hear (via a speaker or through earphones) the differences in vibration amplitude between the two like devices and determine which of the devices has a mechanical fault.

In 1989, JS Products, Inc. of Las Vegas, Nev. introduced to the automotive maintenance and repair field the "ChassisEAR" as an electronic squeak and rattle finder. This device includes six sensitive piezoelectric microphones mounted in alligator-type clamps available for attachment to a variety of vehicle devices and structural points where excessive vibration may be suspected as an indication of mechanical problems. Electrical leads from the individual clamps are connected to a control box which includes vibration signal conversion circuitry for producing audible signals. The control box also includes switching means for selectively interconnecting each individual clamp microphone to the signal conversion circuitry and thereby selective connection to earphones for use by automotive repairmen in determining through audible signal levels and signal types the location and cause of problem-generated automotive sounds and noises.

It is a principal object of the present invention to provide a new and improved vibration and acoustic sound diagnostic tool for the professional automotive maintenance field to detect with greater sensitivity and accuracy the existence, location and cause of under-chassis, under-hood and under-dash problem sounds and noise.

It is a further object of the invention to provide a new and improved electronic listening tool for the professional automotive mechanic which is capable of discriminating with greater sensitivity abnormal acoustic vibratory signals and sounds forming the noise patterns of automotive vehicle structures and operating parts having mechanical problem faults and to locate the source and cause of such abnormal signals and sounds during normal driving movement of the vehicle.

It is a still further object of the invention to provide a new and improved vibration and acoustic sound diagnostic instrument, with multiple vibration pick-up devices positional for direct contact with under-chassis and under-hood automotive vehicle parts and devices, for locating the source and cause of mechanical problem faults related to such parts and devices, the pick-up devices being coupled through electronic circuitry to an earphone headset for audible vibration sound discrimination and to visual means for indicating changes and peaks in vibration sound level and average values of vibration sound level.

Other objects and advantages of the invention will be apparent to those skilled in the professional automotive maintenance field from the following summary and detailed description of the acoustic vibratory signal and sound diagnostic instrument of the invention taken together with the accompanying drawing figures.

SUMMARY OF THE INVENTION

The present invention relates to an improved electronic acoustic vibratory signal and sound detection and diagnostic tool for the professional automotive maintenance field to detect with greater sensitivity and accuracy the existence, location and cause of under-chassis and under-hood part and device vibration abnormalities. In accordance with the invention one or more (preferably 1 to 6) acoustic vibratory pick-up devices, mounted in alligator clamps and/or shim-type slip sensors, are affixed to automotive parts and devices that are deemed to require diagnosis as presenting actual or potential mechanical faults with the generation of problem sounds and noise. Each vibration pick-up device consists of a miniature microphone of either piezoelectric or "Electret" condenser type which is individually interconnected via electric leads to an electronics housing of the tool.

The electronics housing of the acoustic vibratory sound diagnostic tool of the invention includes: an integrated circuit preamplifier; switch means for individually interconnecting the pick-up devices to the preamplifier; calibration circuitry for the visual means (pointer-type decibel meter) for indicating changes and peaks in vibration sound levels; a multi-point range selector; and frequency curve selector. The electronics housing also includes an integrated circuit operational amplifier electrically interconnected to the preamplifier circuitry and range selector through a volume control device with electromagnetic signal output of the operational amplifier fed to an earphone headset.

The decibel meter visual means for indicating changes and peaks in vibration sound level is mounted to the face side of the electronics housing and is electrically interconnected to a fast-slow response selector whereby in the fast mode the meter reacts quickly to changes in vibration sound level giving an indication of peak sound levels and whereby in the slow mode the meter is dampened and indicates an average value of vibration sound level. A rotary switch operates the range selector and allows the operator (the automotive maintenance mechanic) to select one of seven sound level ranges, each spanning 16 decibels. A weighting curve selector interfaces with the preamplifier circuitry with a "C" curve select position being nearly uniform over the sound frequency range of 32 to 10,000 hertz and with an "A" curve select position responding to sound frequencies in the 500 to 10,000 hertz range, the latter being the frequency range of greatest receptivity for the human ear. The output of the preamplifier section of the electronic listening tool of the invention is provided with a jack receptacle for permitting the interconnection of a cassette recorder-player to the circuitry of the tool. A 9 volt rechargeable battery powers the vibration sound detection and diagnostic tool of the invention.

Through the present invention an improved acoustic vibratory signal and sound diagnostic instrument is provided for professional automotive maintenance personnel, particularly automotive repair mechanics. The instrument is ultrasensitive to vibratory sound types and levels and is thus capable of discriminating with great accuracy the acoustic signals and sounds forming the noise patterns of operating under-chassis and underhood parts and devices of modern-day automotive vehicles. The instrument is thereby most suitable for detecting and locating operating part and device problems which generate vibration sound and noise abnormalities, through the hearing capabilities of the professional mechanic. Sound diagnosis is not only performed by the hearing capabilties of the mechanic operator of the instrument but also by visual observation by the operator of meter indications of vibratory sound levels within selected ranges with instrument adjustability to obtain optimum sensitivity of vibratory sound level readings. Further, vibratory sound and noise diagnosis, to locate the source and cause of mechanical problem faults in automotive vehicles, can be performed during normal driving movement of the vehicles.

BRIEF DESCRIPTION OF THE DRAWING FIGURES

FIG. 1a is a front elevation view of the electronics housing of the acoustic vibratory signal and sound diagnostic instrument of FIG. 1 showing in greater detail the sound range controls and visual sound level meter of the instrument;

FIG. 1b is a right side elevation view of the electronics housing of the instrument of FIG. 1a showing the volume control, on-off switch and battery compartment;

FIG. 1c is a left side elevation view of the electronics housing of the instrument of FIG. 1a showing particularly the six jack receptacles for interconnecting the vibration pick-up devices and the electronics housing;

FIG. 1d is bottom view of the electronics housing of the instrument of FIG. 1a showing the six selector switches for individually interconnecting the vibration pick-up devices to the preamplifier of the instrument.

DETAILED DESCRIPTION OF A PREFERRED EMBODIMENT OF THE INVENTION

Figure 1:
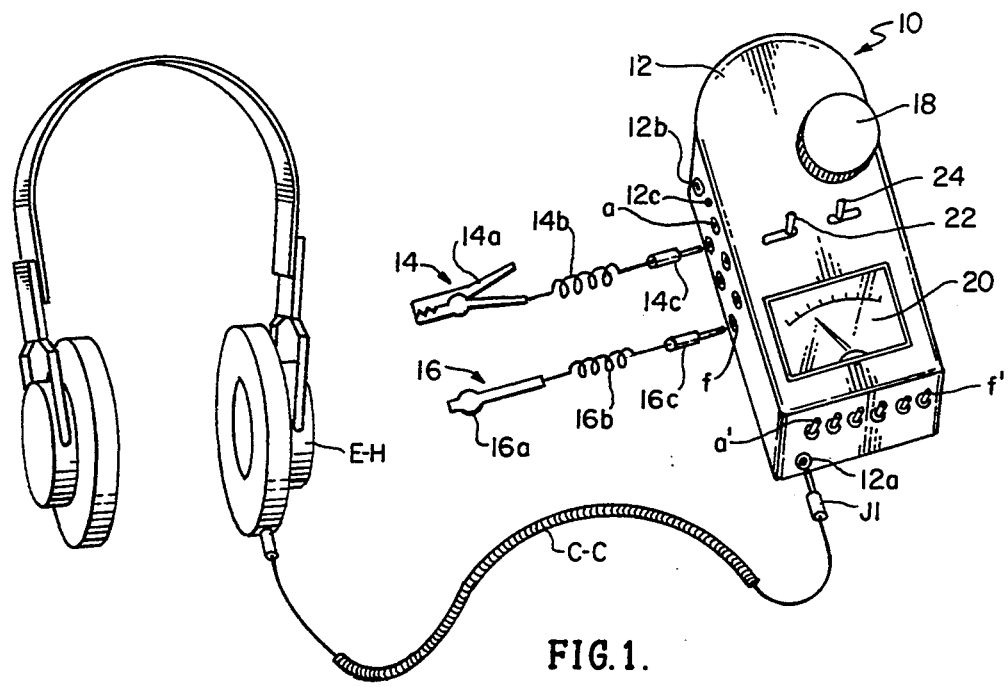
FIG. 1 is a perspective view of the acoustic vibratory signal and sound diagnostic instrument (with an associated earphone headset) of the present invention showing two forms of vibration pick-up devices for interconnection to under-chassis and under-hood parts and devices of an automotive vehicle.

Turning now to the drawings, and initially to FIG. 1, the acoustic vibratory signal and sound diagnostic instrument of the present invention is shown in a perspective view and generally designated as a whole by reference numeral 10. The instrument 10 is comprised of an electronics housing 12 into which may be coupled to one or more acoustic vibratory pick-up devices 14 mounted in alligator clamps 14a and one or more vibratory pick-up devices 16 mounted in shim-type slip sensors 16a. Coupling of the pick-up devices 14 and 16 to the housing 12 is accomplished via extended electric leads 14b and 16b, respectively, and their respective plug-in jacks 14c and 16c.

The electronics housing 12 of the acoustic vibratory signal and sound diagnostic instrument 10 of the invention is preferably of a shape and size such that it can be easily held in the hand of the mechanic operator. As shown in its perspective view in FIG. 1, the front face of electronics housing 12 includes a thumb operated rotatable sound level range selector control 18, a sound level decibel (dB) meter 20, a two position weighting selector control switch 22, and a two position response selector control switch 24. The electronics housing 12 of the instrument 10 (and its internal circuitry as described hereinafter) is interconnected to an earphone headset E-H via a coiled cable C—C and cable jack J1 which is plugged into the jack receptacle 12a of the housing 12.

A more detailed view of the front face of electronics housing 12 is shown in FIG. 1a. The rotatable range selector control 18 allows the operator to select one of seven sound levels, each spanning 16 dB. As shown in FIG. 1a the range selector 18 is in its "off" position and may be rotated clockwise in steps first to a battery "on" (and battery check) position followed by the seven center-point range value settings 120, 110, 100, 90, 80, 70 and 60 dB). The needle indicator of the sound level decibel meter 20 shows the actual vibration sound level as a displacement from the center-point of the meter scale. Thus, for example, if the range selector 18 is set to 80 dB, and the meter scale reads −3, the actual sound level is 80 minus 3 or 77 dB.

The two position response selector control switch 24 has a slow position "S" and a fast position "F". With the response selector switch 24 in the slow position "S" the decibel meter 20 is damped and indicates an average-value vibration sound level. With the switch 24 in the fast position "F" the decibel meter reacts quickly to a change in vibration sound level giving the operator an immediate visual indication of peak vibration sound levels present at the point at which the vibration pick-up device (type 14 or type 16 then coupled into the electronic circuitry of the instrument) is affixed to a part or device of the automotive vehicle undergoing vibration problem diagnosis. The two position weighting curve selector control switch 22 has an "A" curve position and a "C" curve position. In the "C" curve position the C-weighting curve is nearly uniform over the sound frequency range of 32 to 10,000 Hz thus giving an indication of overall vibratory sound level. In the "A" curve position the A-weighting characteristic responds primarily to frequencies in the 500 to 10,000 Hz range which is the area of greatest sensitivity of the human ear.

Figure 2:
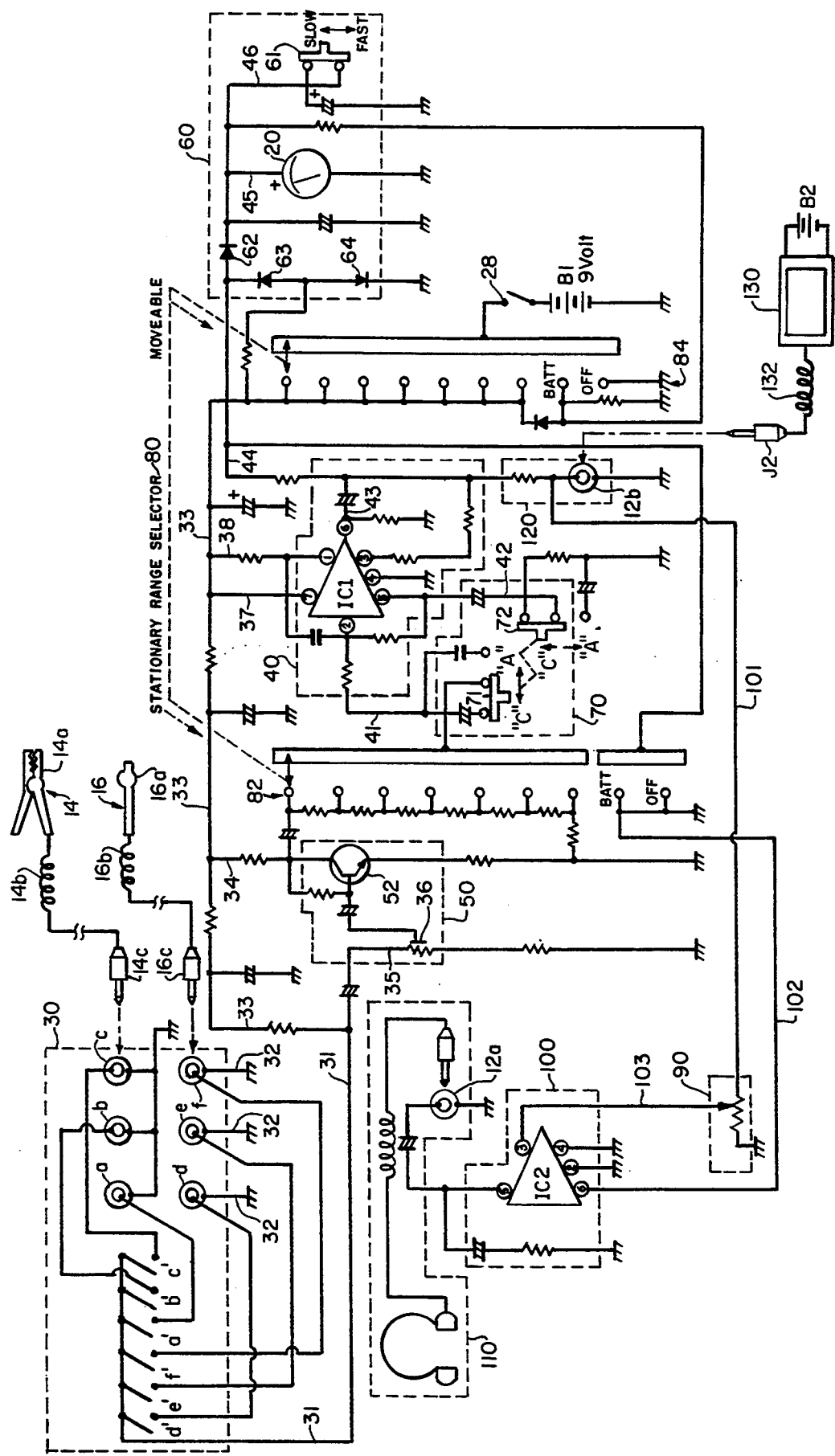
FIG. 2 is an electrical schematic circuit representation of the electronic acoustic vibration signal and sound diagnostic instrument of the invention.

In FIGS. 1b and 1c right side and left side elevation views, respectively, are shown of the electronics housing 12. In the FIG. 1b right side elevation view there is shown a thumb operated rotatable volume controller 26 for regulating the sound volume level transmitted by the sound diagnostic instrument 10 to the earphone headset E-H which is worn by the mechanic operator of the instrument and which is interconnected to the electronics housing 12 via coiled cable C—C. In such figure there is also shown an "on-off" system switch 28 for the instrument. In the FIG. 1c left side elevation view there is shown a jack receptacle 12b for receiving a jack j2 which may be utilized to interconnect a cassette-type recorder-player unit to the sound output circuitry within the electronics housing 12 as shown in FIG. 2. Receptacle 12b may also be used with a cassette adaptor so that sound output from the instrument may be played through the vehicle's own speakers. In such figure there is also shown an access port 12c through which a calibrating tool may be inserted to adjust the instrument, if required. In both FIGS. 1b and 1c there is shown the right and left ends, respectively, of the battery compartment cover 12d which removably closes the battery compartment containing the 9-volt battery power supply for the sound diagnostic instrument 10 of the invention.

As shown particularly in FIGS. 1a, 1b and 1c, there are positioned on the left side of the electronics housing 12, six jack receptacles a, b, c, d, e and f for receiving any combination of six input jacks 14c and/or 16c from vibratory pick-up devices 14 and/or 16 located at selected vibration sensing points on under-chassis and under-hood automotive parts and devices for diagnosis of mechanical problem faults of a vehicle. These views also show the six "on-off" switches a', b', c', d', e' and f' which are selectively used to connect the pick-up devices 14 and/or 16 with the preamplifier circuitry of the electronics housing 12.

Referring now to FIG. 2, there is illustrated an electrical schematic circuit representation of the electronic vibration and acoustic signal and sound diagnostic instrument of the present invention. The principal functional areas of circuitry are outlined by numbered dashline enclosures as follows:

- 30—Instrument sensor input section with jack receptacles a-f and "on-off" switches a'-f' for the acoustic vibratory pick-up devices 14 and 15.
- 40—Pre-amplifier circuitry located in the electronics housing 12.
- 50—Calibration circuitry located in the electronics housing 12.
- 60—Sound level decibel meter and response selector located on and within the electronics housing 12.
- 70—Weighting curve selector located on and within the electronics housing 12.
- 80—Range selector located on and within the electronics housing 12.
- 90—Volume control located on and within the electronics housing 12.
- 100—Operational amplifier located within the electronics housing 12,
- 110—Headphone and headphone jack located outside of the electronics housing 12,
- 120—Output circuitry and jack receptacle for cassette recorder-player.

The acoustic vibratory pick-up devices 14 and 16 (all of one type or a mix of pick-up device types) are connected to the instrument sensor input section 30 of the vibration and sound diagnostic instrument 10 of the present invention via their respective extended electric leads 14b or 16b and respective plug-in jacks 14c and 16c upon insertion of such jacks into the jack receptacles a-f of instrument section 30. The jack receptacles a-f are electrically interconnected through their respective "on-off" switches a'-f' through leads 31 and 32 (ground leads) to the pre-amplifier circuitry 40, instrument calibration circuitry 50 and circuitry of the stationary terminal set 82 and moveable terminal set 84 of the range selector 80. More specifically, the calibration circuitry 50 (including npn bipolar transistor 52) is connected to instrument sensor input circuitry lead 31 via circuit line 33 and lead 34 and via circuit line 35 to the variable resistor 36 of the calibration circuitry 50 and thereafter to ground. Circuit line 33 also connects the integrated circuit microchip IC1 of the pre-amplifier circuitry 40 (via leads 37 and 38) to the sensor input section 30. Finally, circuit line 33 connects the sensor input section 30 to the battery "on" contact and seven switch position contacts of the moveable terminal set 84 and the battery "on" contact and seven switch position contacts of the stationary terminal set 82 of the range selector 80. S The pre-amplifier circuitry 40 interacts with the weighting curve selector 70 through leads 41 and 42 from the microchip IC1 with the weighting curve selector switch 22 (see FIG. 1a) moving the switch contacts 71 and 72 from switch terminals "A" to switch terminals "C". The pre-amplifier circuitry 40 also interacts with the sound level decibel meter and response selector circuitry 60 via circuit lines 43 and 44 from the microchip IC1. When the response selector 61 is in the "Slow" position the decibel meter 20 is damped and indicates an average-value vibratory sound level whereas when the selector 61 is in the "Fast" position the meter 20 reacts quickly to a change in sound level giving an indication of peak sound levels provided by the sensor input section 30. The decibel meter is connected to circuit line 44 of the pre-amplifier circuitry via lead 45 with the response selector 61 interconnected to circuit line 44 via lead 46. The sound level decibel meter and response selector circuitry 60 also includes rectifiers 62, 63 and 64.

A 9 volt battery B1 energizes the electronic circuitry within the electronics housing 12 when the instruments system "on-off" switch 28 is closed. The pre-amplifier circuitry 40, calibration circuitry 50 and range selector circuitry 80 are electrically interconnected to operational (audio) amplifier circuitry 100 via circuitry lines 101 and 102. Circuitry line 101 interconnects to the integrated circuit microchip IC2 of the operational amplifier circuitry 100 via lead 103 through the volume control 90. Circuitry line 102 interconnects directly to the microchip IC2 of the amplifier circuitry 100. The audio signal output of operational amplifier circuitry 100 feeds the headphone and headphone jack unit 110 which includes headphone jack receptacle 12a, located in the electronics housing 12 of the acoustic vibratory sound diagnostic instrument 10 of the invention, and into which the jack J1 may be plugged with interconnection to earphone headset E-H via elongated coiled cord C—C.

It will be noted that the circuitry line 101 leading from the pre-amplifier circuitry 40 to the volume control 90 and operational amplifier 100 includes output circuitry 120 and jack receptacle 12b (located in the electronics housing 12). This output circuitry provides access to the vibration created sound patterns and sound levels picked up by the acoustic vibratory pick-up devices 14 and/or 16 feeding into sensor input section 30 of the instrument 10 for recordation via a cassette type recorder-player unit 130 interconnected to jack receptacle 12b via a coiled cord 132 and jack connector J2. Energization of the recorder-player unit 130, for replay of the recorded vibration sound patterns, may be a battery B2 or by connection of the unit 130 to the low voltage output of an automobile cigarette lighter.

Through the present invention acoustic vibratory signals and sounds generated by under-chassis and under-hood automotive parts and devices having mechanical problem faults can be detected, located and diagnosed with greater sensitivity and accuracy. The diagnostic instrumentation of the invention permits accurate audible sound discrimination and diagnosis through an earphone headset worn by a professional maintenance operator and by visual decible meter means indicating with great sensitivity changes and peaks in vibratory sound level and average values of vibratory sound level generated by abnormalities in automotive part and device operation.

It is to be understood that the vibration and acoustic sound diagnostic instrumentation of the invention permits (through "on-off" switch activation of the acoustic vibratory pick-up devices located on numerous automotive under-chassis and under-hood parts and devices) vibratory sound diagnosis of single point abnormal vibrations. It is also to be understood that the "on-off" switches interconnecting the vibratory pick-up devices with the preamplifier circuitry section of the instrumentation can be all or in part switched to their "on" positions so that multiple (superimposed) vibratory sound patterns can be received by the instrumentation and abnormal vibrations located and diagnosed by subsequent selective termination of the switch connection of such devices with the instrumentation.

While a preferred embodiment of the present invention has been disclosed herein and illustrated in the accompanying drawing figures, it will be apparent to one skilled in the art that many variations and modifications may be made without departing from the scope and spirit of the invention as defined by the following claims.

What I claim is:

1. A vibration and acoustic sound diagnostic instrument for use by an automotive maintenance mechanic for discriminating audible vibration sounds generated by automotive devices having mechanical faults, said instrument comprising:
   a) at least one acoustic vibration pick-up device mounted in contact with an automotive device for detecting and converting audible vibratory acoustic sounds generated by said automotive device into electromagnetic signals;
   b) an electronics housing conformed to be held in the hand of said maintenance mechanic;
   c) pre-amplifier circuitry within said housing electrically coupled to said acoustic vibration pick-up device for receiving said electromagnetic signals from said pick-up device;
   d) range selector circuitry within said housing electrically interconnected to said pre-amplifier circuitry for selecting sound ranges respecting said electromagnetic signals;
   e) a decibel meter mounted to the exterior of said housing and electrically interconnected to said pre-amplifier circuitry for visually indicating changes and peaks in the audible vibratory acoustic sounds detected by said acoustic vibration pick-up device mounted to said automotive device;
   f) operational audio amplifier circuitry within said housing electrically interconnected to said pre-amplifier circuitry for converting said electromagnetic signals into secondary acoustic signals;
   g) a battery power supply electrically interconnected to said range selector circuitry and said pre-amplifier circuitry for energizing said instrument; and
   h) an earphone headset electrically interconnected to said audio amplifier circuitry for use by said maintenance mechanic wherein said secondary acoustic signals are available to said mechanic for audible discrimination of mechanical faults of said automotive device.

2. The vibration and acoustic sound diagnostic instrument as claimed in claim 1 wherein the pre-amplifier circuitry has associated therewith a weighting curve selector with a "C" curve select position which is substantially uniform over the sound frequency range of from 32 to 10,000 Hz and with an "A" curve select position providing maximum sensitivity of human ear response to frequencies in the 500 to 10,000 Hz range.

3. The vibration and acoustic sound diagnostic instrument as claimed in claim 1 wherein the decibel meter has electrically associated therewith a response selector switch having a first slow position whereby said meter is damped and indicates an average-value of the audible vibratory acoustic sounds detected by said acoustic vibration pick-up device and a second position whereby said meter reacts quickly to a change in the audible vibratory acoustic sounds detected by said pick-up device and indicates a peak level of the audible vibratory acoustic sounds detected by said pick-up device.

4. The vibration and acoustic sound diagnostic instrument as claimed in claim 1 wherein the range selector circuitry interconnected to said pre-amplifier circuitry includes a rotatable control switch having an "off" position for terminating operation of the instrument, a battery "on and check" position for operation of the instrument, and a multiplicity of center-point decibel value range setting positions for selecting sound ranges respecting said electromagnetic signals.

5. The vibration and acoustic sound diagnostic instrument as claimed in claim 4 wherein the center-point decibel value range setting positions of the rotatable control switch of the range selector circuitry are 120, 110, 100, 90, 80, 70 and 60 decibels.

6. The vibration and acoustic sound diagnostic instrument as claimed in claim 1 wherein the pre-amplifier circuitry, electrically interconnected to the operational audio amplifier circuitry, includes access means for interconnecting a recorder-player device for recording the sounds picked up by said at least one acoustic vibration pick-up device.

7. The vibration and acoustic sound diagnostic instrument as claimed in claim 1 wherein there are 1 to 6 acoustic vibration pick-up devices each mounted in contact with an automotive device for detecting and converting audible vibratory acoustic sounds generated by said automotive device, said pick-up devices each including a miniature microphone of the type selected from the group consisting of piezoelectric type microphones and condenser type microphones.

8. The vibration and acoustic sound diagnostic instrument as claimed in claim 7 wherein the acoustic vibration pick-up devices are alligator-type electrical clamps within each of which there is mounted a miniature microphone.

9. The vibration and acoustic sound diagnostic instrument as claimed in claim 7 wherein the acoustic vibration pick-up devices are shim-type electrical slip sensors within each of which there is mounted a miniature microphone.

10. A vibration and acoustic sound diagnostic instrument for use by a professional automotive maintenance mechanic for discriminating audible vibratory acoustic sounds generated by automotive under-chassis and under-hood device abnormalities, said instrument comprising:
   a) one or more acoustic vibration pick-up devices each mounted in contact with an automotive device for detecting and converting audible vibratory acoustic sounds generated by said automotive device into electromagnetic signals;
   b) an electronics housing conformed to be held in the hand of said maintenance mechanic;
   c) pre-amplifier circuitry within said housing and electrically interconnected through "on-off" switches to said acoustic vibration pick-up devices for selectively receiving electromagnetic signals from said pick-up devices;
   d) range selector circuitry within said housing electrically interconnected to said pre-amplifier circuitry and operable by a rotatable control switch having a thumb operated selector dial mounted to the outside of said housing, said rotatable control switch of the range selector circuitry having an "off" position for terminating operation of the instrument, a battery "on and check" position for initiating operation of the instrument, and a multiplicity of center-point decibel value range setting positions for selecting sound ranges respecting said electromagnetic signals;
   e) a decibel meter mounted to the exterior of said housing and electrically interconnected to said pre-amplifier circuitry for visually indicating changes and peaks in the vibratory acoustic sounds detected by said acoustic vibratory pick-up devices mounted to said automotive device;
   f) operational audio amplifier circuitry within said housing electrically interconnected to said pre-amplifier circuitry for converting said electromagnetic signals into secondary acoustic signals;
   g) a battery power supply electrically interconnected to said range selector circuitry and said pre-amplifier circuitry for energizing said instrument when the rotatable control switch of said range selector circuitry is turned to said battery "on and check" position; and
   h) an earphone headset electrically interconnected to said audio amplifier circuitry for use by said maintenance mechanic wherein said secondary acoustic signals are available to said mechanic for audible discrimination of device abnormalities of said automotive device.

11. The vibration and acoustic sound diagnostic instrument as claimed in claim 10 wherein the centerpoint decibel value range setting positions of the rotatable control switch of the range selector circuitry are 120, 110, 100, 90, 80, 70 and 60 decibels.

12. The vibration and acoustic sound diagnostic instrument as claimed in claim 10 wherein the preamplifier circuitry has electrically interconnected therewith a weighting curve selector with a "C" curve select position which is substantially uniform over the sound frequency range of from 32 to 10,000 Hz and with an "A" curve select position providing maximum sensitivity of human ear response to frequencies in the 500 to 10,000 Hz range.

13. The vibration and acoustic sound diagnostic instrument as claimed in claim 10 wherein the preamplifier circuitry, electrically interconnected to the operational audio amplifier circuitry, includes access means for interconnecting a recorder-player device for recording the sounds picked up by said acoustic vibration pick-up devices.

14. The vibration and acoustic sound diagnostic instrument as claimed in claim 10 wherein the operational audio amplifier circuitry is provided with a thumb operated rotatable volume control means exterior of said housing for adjusting the volume of the secondary acoustic signals available to said maintenance mechanic through said earphone headset.

* * * * *